(12) United States Patent
Andrews et al.

(10) Patent No.: US 6,290,723 B1
(45) Date of Patent: Sep. 18, 2001

(54) METHOD OF MAKING A SYNTHETIC TRIGLYCERIDE FILLER MATERIAL

(76) Inventors: Winston A. Andrews, 575 El Capitan Dr., Danville, CA (US) 94526; Gloria R. Dumlao, 1764 Camargo Dr., San Jose, CA (US) 95132; Terry R. Knapp, 915 Sierra Vista Dr., Redding, CA (US) 96001

( * ) Notice: Subject to any disclaimer, the term of this patent is extended or adjusted under 35 U.S.C. 154(b) by 0 days.

(21) Appl. No.: 08/459,721

(22) Filed: Jun. 2, 1995

Related U.S. Application Data

(62) Division of application No. 08/259,474, filed on Jun. 14, 1994.

(51) Int. Cl.⁷ .............................. A61F 2/12; G01N 33/92
(52) U.S. Cl. .................................. 623/7; 623/8; 623/901; 623/926; 436/71
(58) Field of Search .................................. 623/7, 8, 901, 623/926; 436/71

(56) References Cited

U.S. PATENT DOCUMENTS

| | | |
|---|---|---|
| 3,293,663 | 12/1966 | Cronin . |
| 3,665,520 | 5/1972 | Perras et al. . |
| 3,954,102 | 5/1976 | Buuck . |
| 4,197,846 | 4/1980 | Bucalo . |
| 4,205,401 | 6/1980 | Frisch . |
| 4,298,998 | 11/1981 | Naficy . |
| 4,550,720 | 11/1985 | Trick . |
| 4,592,755 | 6/1986 | Penton et al. . |
| 4,605,691 | 8/1986 | Balazs et al. . |
| 4,636,213 | 1/1987 | Pakiam . |
| 4,648,880 | 3/1987 | Brauman . |
| 4,671,255 | 6/1987 | Debrul et al. . |
| 4,694,827 | 9/1987 | Weiner et al. . |
| 4,731,081 | 3/1988 | Tiffany et al. . |
| 4,795,463 | 1/1989 | Gerow . |
| 4,863,470 | 9/1989 | Carter . |
| 4,899,764 | 2/1990 | Gauger et al. . |
| 4,904,260 | 2/1990 | Ray et al. . |
| 4,995,882 | 2/1991 | Destouet et al. . |
| 5,067,965 | 11/1991 | Ersek et al. . |
| 5,101,813 | 4/1992 | Trick . |
| 5,133,742 | 7/1992 | Pinchuk . |
| 5,258,026 | 11/1993 | Johnson et al. . |
| 5,358,521 | 10/1994 | Shane . |
| 5,376,117 | 12/1994 | Pinchuk et al. . |
| 5,391,203 | 2/1995 | Bartlett et al. . |
| 5,407,445 | 4/1995 | Tautvydas et al. . |

FOREIGN PATENT DOCUMENTS

| | | |
|---|---|---|
| 0 177 288 | 4/1986 | (EP) . |
| 2192546 A | 1/1988 | (GB) . |
| WO 93/20780 | 10/1993 | (WO) . |
| WO 94/04095 | 3/1994 | (WO) . |
| WO 94/07434 | 4/1994 | (WO) . |
| WO 94/10937 | 5/1994 | (WO) . |

*Primary Examiner*—Corrine McDermott
*Assistant Examiner*—Choon P. Koh
(74) *Attorney, Agent, or Firm*—Milbank, Tweed, Hadley & McCloy LLP

(57) ABSTRACT

A filler material for a surgically implantable prosthesis comprised of a synthetic triglyceride having a viscosity substantially greater than that of naturally occurring triglycerides is provided. The triglyceride composition is formed of saturated alkyl chains to reduce or limit the potential for oxidation of the alkyl chains to form peroxide groups which adversely affect the biocompatibility of the filler material and the implant. Preferably, the filler material has a viscosity substantially the equivalent of a normal human breast. The synthetic triglyceride filler material may also have a lower viscosity which is a liquid at room temperature for use in inflatable devices. Prostheses containing filler material having the desired viscosity and antioxidation characteristics are also provided as well as a method for preparing the filler material.

9 Claims, No Drawings

METHOD OF MAKING A SYNTHETIC TRIGLYCERIDE FILLER MATERIAL

This is a divisional of copending application Ser. No. 08/259,474; filed on Jul. 14, 1994.

FIELD OF THE INVENTION

This invention generally relates to surgical implants or prostheses, and more particularly to a filler material for implants comprising a flexible shell enclosing a filler material and implants containing the filler material.

BACKGROUND OF THE INVENTION

Surgical implants requiring a filler material, such as breast implants, penile implants, or musculature implants, have conventionally used a silicone gel or a saline solution as the filler material. One of the primary concerns in the design of an implant is to provide a tactile response that is comparable to the tactile response of normal human tissue. Silicone has been the filler material of choice primarily because silicone filled implants provided an adequate tactile response, but the very nature of the silicone filler material also limits the desirability of its tactile properties. Silicone filled implants typically comprise about 10–20% cross-linked silicone which forms an interconnected "sponge" in the implant with the remainder of the filler material being low molecular weight silicone oil. Because of this "sponge", silicone filled implants are stiffer than human tissue, such as breast tissue, and do not provide the same feel as human tissue. Moreover, adverse medical consequences have recently become associated with the use of silicone gel filled implants because it has been discovered that the silicone oil can migrate through the implant shell and the silicone oil is not biocompatible with other human tissues. Therefore, the use of silicone based filler materials has been discontinued in the industry. Saline filled implants have not exhibited any adverse medical consequences when used as a filler material in an implant, but saline is not considered a preferred filler material because of the relatively low viscosity (~1 cp) of such a solution which renders undesirable its tactile properties.

In U.S. Pat. No. 4,995,882 issued to Destouet et al., the rights to which are owned by the assignee herein, naturally occurring, vegetable derived triglyceride oils were proposed for use as a filler material for a breast implant. This represented a dramatic break from the teaching of the prior art and is a good and valuable invention. One of the stated reasons for using a triglyceride oil composition was to take advantage of the radiolucent characteristics thereof so that a useful mammogram could be performed of an implanted breast. Although this radiolucency characteristic is important for mammograms, the naturally occurring triglyceride oil compositions disclosed by Destouet et al., such as peanut oil and sunflower seed oil, have a relatively low viscosity (~30 cps) and as such do not completely provide the desired tactile response of a normal breast. Furthermore, naturally occurring triglyceride oils typically contain unsaturated and/or polyunsaturated alkyl groups which are susceptible to oxidation. It is known that polyunsaturated fatty acid side chains of triglycerides will react with molecular oxygen to create unstable reduction products such as superoxide and hydrogen peroxide. This is known as lipid peroxidation or rancidification. The reaction forms peroxy lipid radicals and eventually results in the formation of shorter chain compounds such as malondialdehyde, ethane, pentane and 4-hydroxyalkenals, free fatty acids, and the unstable superoxide and peroxide moieties. The free radicals produced as a result of lipid peroxidation are capable of harming cells and cellular components as well as molecular structures essential to the organism. Because of the hydrophobic nature of lipid radicals, it is believed that membrane associated molecules would be most at risk, but other molecular species such as non-oxidized lipids, carbohydrates, lipoproteins and nucleic acids could be damaged. Thus, it is believed that the oxidation of unsaturated alkyl chains on a triglyceride may reduce over time the biocompatibility of naturally occurring triglycerides in an implant.

There is, therefore, room for improvement with a filler material which retains the radiolucent characteristics of a naturally occurring triglyceride oil while also having an improved viscosity and biocompatibility, and implants containing such a filler material.

SUMMARY OF THE INVENTION

The present invention is directed to a filler material for a surgically implantable prosthesis that exhibits the radiolucent characteristics of naturally occurring triglycerides but which also has a greater viscosity and which provides a tactile response substantially the equivalent of the tactile response of normal human tissue, such as breast tissue. According to the invention, a synthetic triglyceride composition containing triglycerides having saturated alkyl chains of between 4 and 26 carbons in length in proportions such that the triglyceride composition has a viscosity substantially greater than naturally occurring triglyceride oils is provided. Preferably, the filler material provides a tactile response substantially the equivalent of the tactile response of normal human tissue, and has a viscosity of about 10,000 cps at a temperature of between about 32° C. and about 40° C. Its viscosity can be compared to that of a viscous paste over the extremes of physiologic temperature, i.e. 32° C. to 40° C. This is achieved by providing a triglyceride composition having alkyl chains of varying lengths in selected proportions to provide this increased viscosity characteristic.

In another aspect of the invention, the filler material is prepared in a manner which reduces its susceptibility to autoxidation to enhance its biocompatibility. This is achieved by utilizing triglycerides that have substantially all saturated alkyl groups or by the inclusion of antioxidants with the filler material.

In still another aspect of the invention, a surgically implantable prosthesis containing a filler material that can be provided in a range of viscosities, and a method for preparing such a filler material, is provided. This enables the provision and production of an implant having a pre-selected viscosity or tactile response.

In yet another aspect of the invention, a synthetic triglyceride composition containing triglycerides having fully saturated fatty acid (alkyl) side chains in proportions providing a composition that is a liquid at room temperature (~23° C.) is provided. This filler material has a viscosity similar to that of naturally occurring triglyceride oils, but is fully saturated to limit the possibility of oxidation and can be readily injected via a small diameter delivery tube into an already implanted device.

The present invention is further directed to surgically implantable prostheses containing this filler material within the sealed shell of the prosthesis.

DETAILED DESCRIPTION OF THE PREFERRED EMBODIMENTS

In accordance with the present invention, a filler material for a surgically implantable prosthesis comprising a synthetic triglyceride composition is provided. The triglyceride composition is preferably resistant to oxidation by the provision of fully saturated alkyl chains on the triglycerides and the triglyceride composition contains alkyl chains (fatty acid side chains) of varying lengths in a selected proportion such that the triglyceride composition has a viscosity of at least about 10,000 cps at a temperature of between about 32° C. and 40° C.

Fully saturated alkyl chains from fatty acids of the desired carbon chain length are utilized in the preparation of the triglyceride filler material of this invention to reduce or eliminate the vulnerability of the triglyceride composition to oxidation which can result in the production of free radicals which reduce the biocompatibility of the filler material and could have adverse effects on surrounding tissue in the event of leakage or implant rupture. While it is preferred that the alkyl chains be fully saturated for these reasons, synthetic triglyceride compositions that are substantially saturated are effective in limiting the oxidation of the composition and represent a significant improvement over naturally occurring triglycerides that are typically highly unsaturated. It is preferable if the alkyl groups are at least about 80% saturated, and more preferably greater than 90% saturated. To further limit the possibility of oxidation of a triglyceride composition, antioxidants such as tocopherol (Vitamin E) can be added to the composition.

The triglyceride composition of the present invention can be prepared using standard methods known to those skilled in the art such as by reacting pure, fully saturated fatty acids of the desired carbon length with purified glycerol in an esterification reaction. The resulting triglyceride is purified from the reaction mixture by known techniques to provide a pure, non-contaminated triglyceride. Fatty acids varying in length from 4 carbons to at least 26 carbons may be advantageously used in this reaction to form a triglyceride having alkyl chains of the desired length. The reaction mixture may contain only a single fatty acid of a desired chain length or the reaction mixture may contain a mixture of fatty acids of different lengths. Preferably, saturated fatty acids of varying carbon length are provided in pre-selected proportions to yield a triglyceride composition having a selected viscosity.

Alternatively, triglycerides can be prepared with only a single carbon length fatty acid and the filler material of the present invention is obtained by blending different triglycerides, each presenting alkyl chains of a uniform chain length, in such a manner as to provide a blend of triglycerides containing a mixture of alkyl chain lengths having the selected viscosity. When this method is employed, it must be understood that the proportions of the different carbon chain lengths needed to obtain the selected viscosity, as compared to the proportions needed to obtain a composition having the same viscosity by the preferred method, are not necessarily identical because of the differences in the structure of the compositions.

In the preparation of a triglyceride composition of a selected viscosity, a composition having a known proportion of alkyl chain lengths is prepared and the viscosity and tactile response of the composition in the appropriate temperature range is determined. If the resulting composition does not have the selected or desired viscosity or tactile response, the alkyl chain length proportions are varied and a new composition prepared and analyzed.

By preparing a triglyceride composition in accordance with the method of this invention, an implant containing a filler material of a desired or pre-selected viscosity can be provided by adjusting the proportions of the varying lengths of alkyl chains on the triglycerides. If a more viscous composition having a "stiffer" tactile response is desired, a higher proportion of longer carbon chains and a higher average molecular weight, e.g. 10–14 carbon length fatty acids, can be used. If a less viscous composition having a more fluid tactile response is desired, a higher proportion of shorter carbon chains and having a lower average molecular weight, e.g. 6 or 8 carbon length fatty acids, can be used. By preparing triglyceride compositions according to the method described above using different proportions of fatty acids of varying carbon chain length, an array of triglyceride compositions having different viscosities and tactile properties can be determined. This provides a consumer with a choice among implants having a range of viscosities and permits the selection of an implant containing a filler material of a selected viscosity and tactile response.

It should be understood that triglyceride compositions containing saturated alkyl chains of the desired length can also be purchased commercially and blended in the selected proportions to obtain a composition of the selected viscosity.

The triglyceride composition of this invention preferably has a viscosity substantially greater than that of naturally occurring triglyceride oils, such as the peanut oil and sunflower seed oil triglycerides disclosed by Destouet et al. Naturally occurring triglycerides, especially the vegetable triglycerides disclosed in Destouet et al., typically have a viscosity of approximately 30 cps. The filler material of the present invention preferably has a viscosity between about 10,000 cps and about 50,000 cps, in a temperature range of between about 32° C. and about 40° C., and more preferably between about 10,000 cps and 20,000 cps. The viscosity of a triglyceride composition of this invention is measured by conducting a standard viscosity test known to those skilled in the art, such as the rotating spindle procedure, or by the measurement of the flow of the fluid compared to a known standard, the flow being inversely proportional to its viscosity. It has been found that a synthetic triglyceride composition having a viscosity in the preferred range provides a tactile response substantially the equivalent of normal human tissue, and in particular, normal human breast tissue.

As described, the triglycerides used in the triglyceride composition of the present invention may contain alkyl chains varying in length from 4 carbons to 26 carbons in proportions which provide the desired viscosity. The triglycerides are of the formula

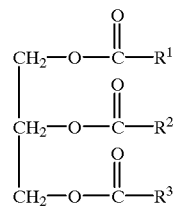

where $R^1$, $R^2$, and $R^3$ are independently selected from alkyl chains of between 4 and 26 carbons in length. To determine whether a particular proportion of triglycerides of differing alkyl chain lengths in a triglyceride composition is sufficient for use in this invention, a desired combination is prepared and its viscosity measured at around body temperature, approximately 37° C. If the tested composition exhibits a viscosity of about 10,000 cps, it is considered suitable for use as a filler material in accordance with the present invention. It is believed that by preparing a triglyceride composition having a blend of alkyl chains of varying length in the desired proportional amounts, a coincidence of melting points of the various triglycerides is achieved which results in a composition having the desired viscosity. A triglyceride composition of this invention preferably comprises a blend of at least three triglycerides containing alkyl chains of between 6 and 14 carbons in length. A particular preferred triglyceride composition suitable for use in the present invention has been prepared and contains triglycerides having about 8% eight carbon saturated alkyl chains, about 8% ten carbon saturated alkyl chains, and about 84% twelve carbon saturated alkyl chains. This synthetic triglyceride composition has a viscosity of about 15,000 cps at 3° C., has a consistency similar to "warm butter" and closely approximates the tactile properties of a normal human breast.

In another exemplary synthetic triglyceride composition, a triglyceride composition having a viscosity that provides a more "fluid" tactile response has been prepared by producing a composition having about 15% six carbon saturated alkyl chains, about 15% eight carbon saturated alkyl chains, and about 70% ten carbon saturated alkyl chains in the overall triglyceride composition. This composition has a viscosity of about 10,000 cps at 37° C.

In an alternate embodiment of the invention, a synthetic triglyceride composition having a lower average molecular weight as a result of reduced average fatty acid side chain length and which is a liquid at room temperature is provided which is suitable for use in inflatable devices. This filler material is prepared from fully saturated fatty acids as previously described and provides a filler material that has a viscosity of approximately 30–100 cps. This filler material, therefore, has a viscosity similar to the viscosity of naturally occurring triglyceride oils, but is not as vulnerable to oxidation (as previously described). Because this embodiment is a liquid at room temperature, it can readily be injected via a small diameter delivery tube into a previously implanted inflatable-type device. An exemplary synthetic triglyceride composition of this embodiment contains triglycerides having about 10% eight carbon saturated alkyl chains, about 60% ten carbon saturated alkyl chains, and about 30% twelve carbon saturated alkyl chains. This filler composition has a viscosity of about 30 cps, similar to naturally occurring triglyceride oils, but contains fully saturated alkyl chains and is thereby resistant to oxidation in contrast to naturally occurring triglyceride oils. The filler material previously described having a viscosity of about 10,000 cps is a solid at room temperature which must be heated to higher than physiological temperatures (e.g. 40° C.–43° C.) to liquify the filler material for introduction into an implanted inflatable device via a small tube. Thus, the first embodiment of the triglyceride composition as previously described can be used with inflatable devices, but requires the introduction technique to be revised by preheating the filler material in its container to reduce its viscosity for introduction. When this method is employed, care must be taken not to increase the temperature of the composition too much as damage to surrounding tissues could occur during introduction into the device.

Both embodiments of the filler material are suitable for use in implantable prostheses of the type comprising a sealable shell or envelope. Techniques for manufacturing and filling this type of prosthesis are well known to those of ordinary skill in the art and may be used herein. Thin walled shells comprised of a silicone polymer as well as other known shell materials are suitable for use in combination with the filler material of this invention. As described, the shells may be of the type that are pre-filled or that may be filled after implantation through small diameter delivery tubes.

Just as prior art filler materials have been found to migrate through shells made of semi-permeable membranes such as silicone polymers, the filler material of the present invention is expected to do the same. However, with filler material of the present invention, higher molecular weight carbon chains may be employed and the larger carbon chains will minimize the amount of filler material which does migrate. Health risks associated with migration of filler material are thus expected to be reduced or even eliminated.

It is to be understood that various changes and modifications which may be made to the invention as would be apparent to those skilled in the art are considered to be included in the teaching of the disclosure, and it is intended that the invention be limited only by the scope of the claims appended hereto.

What is claimed is:

1. A method for preparing a synthetic triglyceride filler material of a pre-selected viscosity for use in a surgically implantable prosthesis, the method comprising:

selecting a viscosity for the synthetic triglyceride filler material; and formulating a synthetic triglyceride filler material composition having synthetic triglycerides comprised of alkyl chains of varying length in proportional amounts sufficient to yield a filler material of the selected viscosity.

2. The method of claim 1 wherein the synthetic triglyceride filler material is formulated by reacting proportional amounts of fatty acids of different chain lengths with glycerol in an esterification reaction to yield the synthetic triglyceride filler material of the pre-selected viscosity.

3. The method of claim 1 wherein the synthetic triglyceride filler material composition is formulated by obtaining synthetic triglycerides of different alkyl chain length and mixing said triglycerides together in proportional amounts to yield the synthetic triglyceride filler material of the pre-selected viscosity.

4. The method of claim 2 wherein the viscosity elected provides a tactile response substantially the equivalent of the tactile response of a normal human breast.

5. The method of claim 4 wherein the fatty acids are between 4 and 26 carbons in length.

6. The method of claim 5 wherein three fatty acids of between 6 and 14 carbons in length are selected and provided in proportional amounts to yield a filler material having a viscosity of at least about 10,000 cps when reacted with glycerol.

7. The method of claim 3 wherein the viscosity selected provides a tactile response substantially the equivalent of the tactile response of a normal human breast.

8. The method of claim 7 wherein the fatty acids are between 4 and 26 carbons in length.

9. The method of claim 8 wherein three fatty acids of between 6 and 14 carbons in length are selected and provided in proportional amounts to yield a filler material having a viscosity of at least about 10,000 cps when reacted with glycerol.

* * * * *